US008682813B2

(12) United States Patent
Yuta

(10) Patent No.: US 8,682,813 B2
(45) Date of Patent: Mar. 25, 2014

(54) SAMPLE CLASS PREDICTION METHOD, PREDICTION PROGRAM, AND PREDICTION APPARATUS

(75) Inventor: Kohtarou Yuta, Narashino (JP)

(73) Assignee: Fujitsu Limited, Kawasaki (JP)

( * ) Notice: Subject to any disclaimer, the term of this patent is extended or adjusted under 35 U.S.C. 154(b) by 357 days.

(21) Appl. No.: 13/019,683

(22) Filed: Feb. 2, 2011

(65) Prior Publication Data

US 2011/0137841 A1 Jun. 9, 2011

Related U.S. Application Data

(63) Continuation of application No. PCT/JP2008/064058, filed on Aug. 5, 2008.

(51) Int. Cl.
*G06K 9/62* (2006.01)
*G06F 19/00* (2011.01)

(52) U.S. Cl.
CPC ............ *G06K 9/6286* (2013.01); *G06K 9/6256* (2013.01); *G06K 9/6234* (2013.01); *G06F 19/704* (2013.01); *G06F 19/707* (2013.01)
USPC .............................................. 706/12; 703/12

(58) Field of Classification Search
CPC .. G06K 9/6234; G06K 9/6256; G06K 9/6286
See application file for complete search history.

(56) References Cited

U.S. PATENT DOCUMENTS 5,796,632 A 8/1998 Yuta
7,725,413 B2 5/2010 Yuta

FOREIGN PATENT DOCUMENTS

| JP | 5-143636 | 6/1993 |
|----|----------|--------|
| JP | 8-123781 | 5/1996 |
| JP | 2002-73076 | 3/2002 |
| JP | 2004-86897 | 3/2004 |
| WO | 2008/059624 A1 | 5/2008 |

OTHER PUBLICATIONS

Duda, R. O., Hart, P. E. & Stork, D. G. Pattern Classification. (Wiley-Interscience: 2001). Excerpt of pp. 215-239, with 2 pages of front matter.*
StatSoft. Discriminant Function Analysis. 1-6 (2003). From <http://www.statsoft.com/textbook/stdiscan.html>, accessed Jan. 21, 2006. 6 pages.*
Timm, N. H. Applied Multivariate Analysis. (Springer-Verlag: New York, New York, USA, 2002). Excerpt of pp. 419-428, with 2 pages of front matter.*
International Search Report for PCT/JP2008/064058, mailed Nov. 18, 2008.

* cited by examiner

*Primary Examiner* — Soren Harward
(74) *Attorney, Agent, or Firm* — Staas & Halsey LLP

(57) ABSTRACT

To predict the class of an unknown sample, a) a discriminant function for assigning each training sample to class 1 or class 2 is obtained, b) the discriminant score of each training sample and an unknown sample are calculated using the function, c) it is determined whether the score of the unknown sample is either not smaller than the largest score or not larger than the smallest score taken among all of the training samples, d) if the determination in c) is affirmative, the class of the unknown sample is determined based on the score of the unknown sample, e) if the determination in c) is negative, then the training samples having the largest score and the smallest score are removed to form a new training sample set from remaining training samples, and f) a) to e) are repeated.

18 Claims, 9 Drawing Sheets

Fig.6
| | A<br>Structure | B<br>CAS Number | C<br>Ames test |
|---|---|---|---|
| 1 | 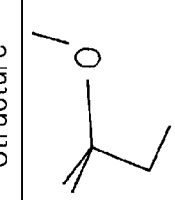 | 994-05-8 | nonmutagen (−) |
| 2 | 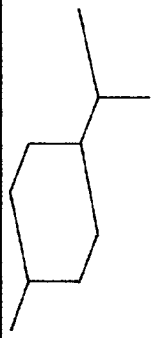 | 99-82-1 | nonmutagen (−) |
| 3 | 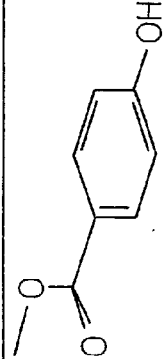 | 99-76-3 | nonmutagen (−) |
| 4 | 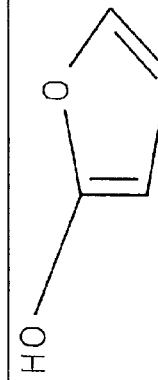 | 98-00-0 | mutagen (+) |
| 5 | 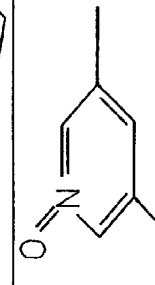 | 97-56-1 | mutagen (+) |

Fig.7

| | A Structure | B Molecular Mass (Whole Molecule) | C Molecular Surface Area (Whole Molecule) | D Molecular Volume (Whole Molecule) | E Kappa 1 index (Whole Molecule) | F log P (Whole Molecule) | G Shape Flexibility index (Whole Molecule) | H Randic Topological index (Whole Molecule) |
|---|---|---|---|---|---|---|---|---|
| 1 | | 102.2 (x11) | 143.704 (x21) | 91.8144 (x31) | 7 | 1.3154 | 2.30088 | 3.12132 |
| 2 | | 140.3 (x12) | 190.412 (x22) | 129.174 (x32) | 8.1 | 3.7656 | 2.76071 | 4.69838 |
| 3 | | 152.16 (x13) | 172.868 | 101.168 | 9.09091 | 1.4923 | 2.35543 | 5.23638 |
| 4 | | 98.11 (x14) | 120.712 | 68.9598 | 5.14286 | 0.4597 | 1.24264 | 3.43185 |
| 5 | | 123.17 (x15) | 152.166 | 89.6854 | 7.11111 | 0.9371 | 1.48936 | 4.18154 |

SAMPLE CLASS PREDICTION METHOD, PREDICTION PROGRAM, AND PREDICTION APPARATUS

CROSS REFERENCE TO RELATED APPLICATION

The present application is a continuation application based on International Application No. PCT/JP2008/064058, filed on Aug. 5, 2008, the entire contents of which are incorporated herein by reference.

FIELD

The present invention relates to a method, program, and apparatus for predicting the class to which a sample whose class is unknown belongs.

BACKGROUND

A typical example of a classification problem is the problem of character recognition. The current level of data analysis in character recognition is extremely high, and generally, recognition rates of 99% or higher can be achieved. On the other hand, in a two-class classification problem for chemical toxicity (hereinafter, safety) evaluation, which has come to attract attention in recent years because of environmental problems, etc., the prediction rate and classification rate that can be achieved are much lower than those achievable in the character recognition problem. Usually, the best achievable classification rate is said to be around 80% to 90%, and the limit of the prediction rate is said to lie in the range of 70% to 80%. The major reasons are that the factors contributing to the manifestation of toxicity of chemicals are complex and diverse, and the structural variety among chemicals is enormous. However, the safety evaluation of chemicals is an extremely important problem; if the classification or the prediction is wrong, in particular, if a toxic chemical is wrongly classified or predicted as a safe chemical, it will have a serious impact on society. From this point of view, it is strongly desired to improve the accuracy of classification/prediction in the safety evaluation of chemicals.

For these reasons, it is now recognized that increasing the classification rate is an issue of utmost importance in chemical classification problems, and various efforts have been expended for this purpose. The present inventor has proposed a method that can achieve classification rates as close as possible to 100%, that is, "K-step Yard sampling method" (hereinafter referred to as the KY method) (refer to patent document 1 and non-patent document 1).

In this method, first a training sample set is classified by discriminant analysis into two groups, i.e., a group of samples each of which is clearly known to belong to class 1 or class 2, and a group of samples (gray class samples) for which the class each belongs is not clearly known. In the group of samples whose classes are clearly known, each sample is assigned to the class determined based on the result of the discriminant analysis; on the other hand, in the case of the gray class sample group, a new training sample set is constructed using the gray class samples, and discriminant analysis is performed once again. By repeating this process until the number of gray class samples decreases to zero, the classification rate is finally brought to nearly 100%.

The plurality of discriminant functions obtained by performing the KY method are used as a prediction model for predicting the classes of samples whose properties to be classified are unknown. Since this prediction model achieves a classification rate of nearly 100%, a high prediction rate can be expected.

In recent years, a regulation referred to as REACH has entered into force in the EU, and it is expected that a large amount of data on chemical toxicities will be accumulated as its implementation proceeds. Usually, a prediction model is generated by gathering samples whose property values to be predicted are known, i.e., whose dependent variable values are known, and by performing data analysis on the training sample set constructed using these known samples. The larger the number of samples contained in the training sample set, the higher the reliability of the generated prediction model. Therefore, when new data usable as training samples are accumulated after generating the prediction model, it is desirable to generate a new prediction model using a new training sample set constructed by adding the new data.

However, for that purpose, the prediction model has to be updated periodically, which takes a lot of labor and cost. When constructing a prediction model by the above-described KY method, the training sample set needs to be classified by discriminant analysis in many stages and, to generate the prediction model from one training sample set, it takes a great deal of labor and expense compared with the conventional method. Accordingly, if predictions about unknown samples can be made without having to use a prediction model generated based on a fixed training sample set, the classes of the unknown samples can be determined very efficiently. Further, in that case, a higher prediction rate can be expected because the classes of the unknown samples can be predicted based on a training sample set constantly kept up to date by adding new data.

Patent document 1: WO2008/059624

Non-patent document 1: "Development of K-step Yard Sampling Method and its Application to ADME-T Predictions," 34th Structure-Activity Relationships Symposium, November 2006

SUMMARY

Problem to be Solved by the Invention

Accordingly, it is an object of the present invention to provide a sample class prediction method, program, and apparatus that can classify and predict the class of an unknown sample with high accuracy without using any existing prediction model but by using constantly updated new training sample data. Since there is no need to use any existing prediction model, this method is referred to as a model-free prediction model.

Means for Solving the Problem

To achieve the above object, there is provided a sample class prediction method comprising: a) obtaining a discriminant function for performing classification/prediction to assign each training sample in a training sample set to class 1 or class 2 on the basis of a plurality of explanatory variables generated for each training sample; b) calculating a discriminant score for each training sample and a discriminant score for an unknown sample by using the discriminant function; c) determining whether the discriminant score of the unknown sample is either not smaller than the largest discriminant score or not larger than the smallest discriminant score taken among all of the training samples; d) if the determination in c) is affirmative, then determining the class to which the unknown sample belongs in accordance with the discriminant score of the unknown sample; e) if the determination in c) is negative, then removing at least the training sample having the largest discriminant score and the training sample having the smallest discriminant score from the training sample set, and constructing a new training sample set by using remaining training samples; and f) repeating a) to e) for the new training sample set.

To achieve the above object, there is provided a sample class prediction program for causing a computer to execute: a) obtaining a discriminant function for performing classification/prediction to assign each training sample in a training sample set to class 1 or class 2 on the basis of a plurality of explanatory variables generated for each training sample; b) calculating a discriminant score for each training sample and a discriminant score for an unknown sample by using the discriminant function; c) determining whether the discriminant score of the unknown sample is either not smaller than the largest discriminant score or not larger than the smallest discriminant score taken among all of the training samples; d) if the determination in c) is affirmative, then determining the class to which the unknown sample belongs in accordance with the discriminant score of the unknown sample; e) if the determination in c) is negative, then removing at least the training sample having the largest discriminant score and the training sample having the smallest discriminant score from the training sample set, and constructing a new training sample set by using remaining training samples; and f) repeating a) to e) for the new training sample set.

To achieve the above object, there is provided a sample class prediction apparatus for performing data analysis on a training sample set constructed from a plurality of samples, each known to belong to class 1 or class 2, and thereby predicting the class to which an unknown sample, not known to belong to the class 1 or the class 2, belongs, comprising: an explanatory variable generating device which generates explanatory variables for the unknown sample as well as for each training sample contained in the training sample set; a discriminant function generating engine which generates a discriminant function for discriminating between the class 1 and the class 2 by performing discriminant analysis based on the explanatory variables generated for each training sample; a discriminant score calculation device which calculates a discriminant score for each training sample and a discriminant score for the unknown sample by using the generated discriminant function; a discriminant score comparing device which compares the discriminant score calculated for the unknown sample with the discriminant score calculated for each training sample; a class determining device which, based on a result of the comparison made by the discriminant score comparing device, determines the class to which the unknown sample belongs; a sample set generating device which generates a new training sample set by removing, based on the result of the comparison made by the discriminant score comparing device, at least a training sample having the largest discriminant score and a training sample having the smallest discriminant score from the training sample set; and a control device which causes the explanatory variable generating device, the discriminant function generating engine, the discriminant score calculation device, the discriminant score comparing device, the class determining device, and the sample set generating device to operate repeatedly by using the generated new training sample set as the training sample set, and wherein if the result of the comparison made by the discriminant score comparing device indicates that the discriminant score of the unknown sample is either not smaller than the largest discriminant score or not larger than the smallest discriminant score taken among the plurality of training samples, the class determining device determines the class to which the unknown sample belongs in accordance with the discriminant score of the unknown sample.

A discriminant function for performing classification/prediction to assign each training sample to one or the other of the first and second classes can be obtained by discriminant analysis of the training sample set. The discriminant score of each sample calculated by using this discriminant function can be considered a measure of the likely correctness of the classification/prediction. Accordingly, the training sample having the largest discriminant score and the training sample having the smallest discriminant score each provide the most reliable measure in terms of the accuracy of the classification/prediction that is performed according to the sign of the discriminant score.

If the discriminant score calculated for the unknown sample by using the same discriminant function is not smaller than the largest discriminant score or not larger than the smallest discriminant score taken among the plurality of training samples, then the classification accuracy of the unknown sample having such a discriminant score is the same as or higher than the classification accuracy of the training sample having the largest or smallest discriminant score. Therefore, in this case, the class of the unknown sample is determined according to, for example, the sign of its discriminant score.

On the other hand, if the discriminant score of the unknown sample is smaller than the largest discriminant score but larger than the smallest discriminant score taken among the plurality of training samples, the class of the unknown sample is not determined according to its discriminant score, but a new training sample set is constructed by removing at least the training sample having the largest discriminant score and the training sample having the smallest discriminant score from the training sample set. After that, discriminant analysis is performed on the new training sample set. By repeating this process until the discriminant score of the unknown sample becomes equal to or larger than the largest discriminant score or smaller than the smallest discriminant score taken among the plurality of training samples, the classification/prediction of the unknown sample can be made with very high accuracy.

Effect of the Invention

According to the method, program, and apparatus disclosed in this specification, once a training sample set is constructed, the class prediction of an unknown sample can be performed in parallel with the data analysis of the training sample set. Since the process can be performed without having to use any existing classification/prediction model, there is no need to update the classification/prediction model as new training sample data is accumulated. Furthermore, since the classification/prediction of the unknown sample is made based on whether the discriminant score of the unknown sample is larger than the largest discriminant score or smaller than the smallest discriminant score taken among the plurality of training samples, the accuracy of the resulting classification/prediction is quite high.

BRIEF DESCRIPTION OF THE DRAWINGS

FIG. 6 is a diagram depicting one example of a sample data table.

FIG. 7 is a diagram depicting one example of a final parameter set data table.

DESCRIPTION OF REFERENCE NUMERALS

Figure 1:
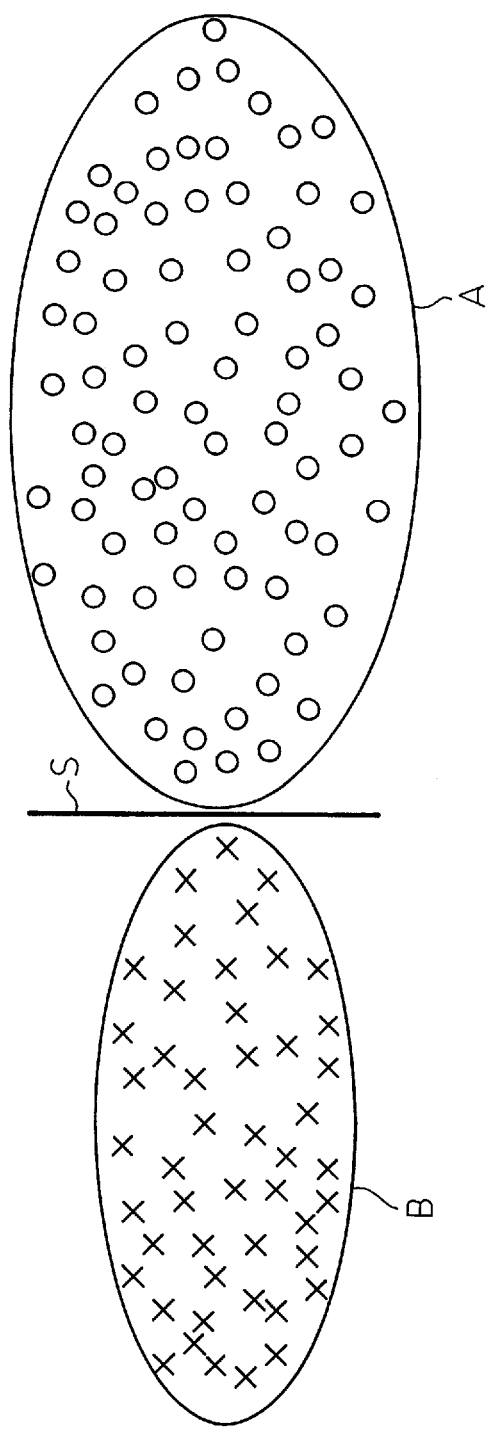
FIG. 1 depicts a pattern space obtained as a result of an ideal two-class classification.

1 . . . misclassified samples of class 1
2 . . . misclassified samples of class 2
100 . . . sample class prediction apparatus
110 . . . input device
120 . . . output device
130 . . . input data table
140 . . . initial parameter set table
150 . . . final parameter set table
160 . . . prediction result storing table
200 . . . analyzing unit
210 . . . initial parameter generating engine
220 . . . control device
230 . . . feature extraction engine
240 . . . discriminant function generating engine
250 . . . discriminant score calculation device
260 . . . sample set generating device
270 . . . analysis termination condition detecting device
280 . . . discriminant score comparing device
290 . . . class assignment determining device
300 . . . sample library

DESCRIPTION OF EMBODIMENTS

Before describing the embodiments of the invention, the principles of the invention will be described below.

FIG. 1 depicts a pattern space obtained as a result of an ideal two-class classification by discriminant analysis. The term, "ideal" means that the classification rate is 100%. In the figure, S indicates a decision surface or hyperplane; region A on the right-hand side of the decision surface S is the region where samples of class 1 are contained (hereinafter referred to as the class-1 region), and region B on the left-hand side is the region where samples of class 2 are contained (hereinafter referred to as the class-2 region). Each white dot indicates a sample that normally belongs to class 1, and each X indicates a sample that normally belongs to class 2.

In the ideal two-class classification, i.e., when the classification rate is 100%, the samples of class 1, indicated by white dots, and the samples of class 2, indicated by Xs, lie on the respectively designated sides of the decision surface S, and the class-1 region A and the class-2 region B do not overlap each other. On the other hand, in a conventional two-class classification, the regions A and B partly overlap each other.

Figure 2:
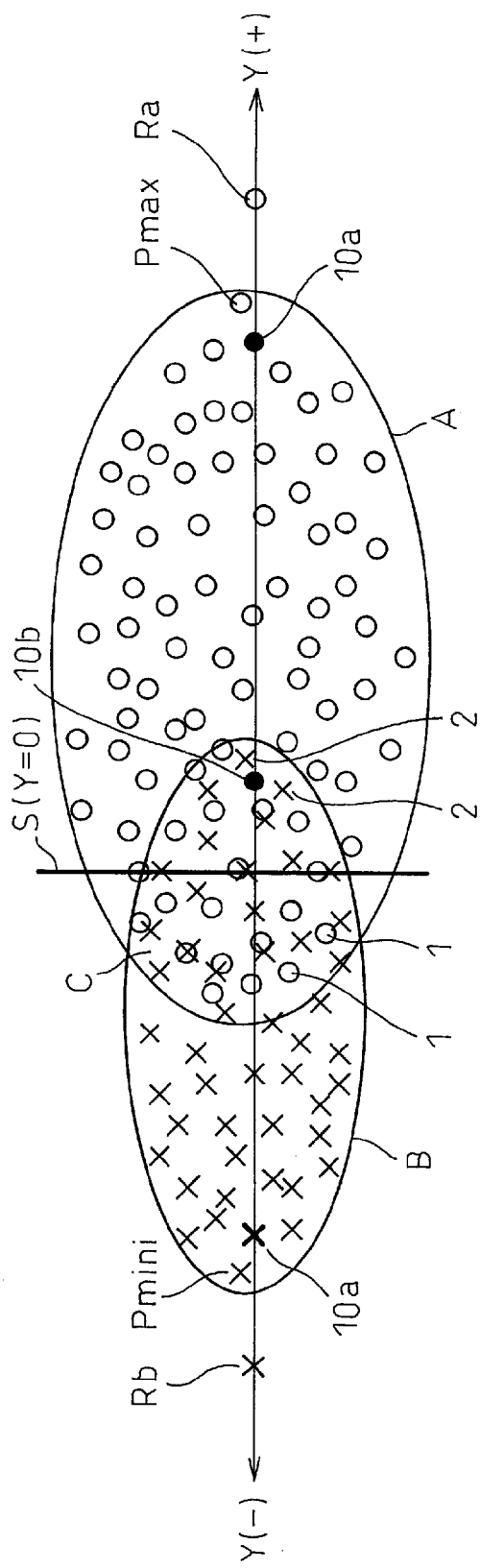
FIG. 2 depicts a pattern space obtained as a result of a conventional two-class classification.

FIG. 2 depicts a pattern space obtained as a result of the conventional two-class classification. When the classification rate falls short of 100%, the regions A and B are not perfectly separated by the decision surface S, and an overlapping region C is formed. As a result, there occur samples 1 which normally belong to class 1 but are located in the class-2 region and thus wrongly classified as samples of class 2, and samples 2 which normally belong to class 2 but are located in the class-1 region and thus wrongly classified as samples of class 1. These wrongly classified samples are called the misclassified samples, and the samples other than the misclassified samples are referred to as the correctly classified samples. The misclassified samples include samples normally belonging to class 1 as well as samples normally belonging to class 2.

A discriminant function (model) Y for discriminating between class 1 and class 2 is expressed by the following equation (1).

$$Y = a_1 x_1 \pm a_2 x_2 \pm \ldots \pm a_n x_n \pm C \qquad (1)$$

In the above equation (1), Y indicates the value of the dependent variable, and $x_1, x_2, \ldots, x_n$ indicate the values of the explanatory variables (parameters), while $a_1, a_2, \ldots, a_n$ are weighting coefficients, and C is a constant. The explanatory variables, $x_1, x_2, \ldots, x_n$, have values different for different samples, while the weighting coefficients, $a_1, a_2, \ldots, a_n$, have values common to all the samples. Usually, the weighting coefficients are chosen so that the value of the dependent variable Y becomes positive for a sample belonging to class 1 and negative for a sample belonging to class 2. In this case, the decision surface S depicted in FIGS. 1 and 2 indicates the plane (hyperplane) where the value of Y is 0.

By substituting the values of the explanatory variables (parameters), $x_1, x_2, \ldots, x_n$, obtained for each sample into the equation (1), the value of the dependent variable, $Y(k)$, is found for each sample. In the discriminant analysis, the value $Y(k)$ is defined as the "response variable" or "dependent variable," but when it is viewed as numerical data, it indicates a "discriminant score" which is a continuous variable. The discriminant score indicates how far the sample is located from the decision surface S in the pattern space.

Usually, in the two-class classification, the discriminant function is constructed so that the discriminant score has a plus (positive) sign for a sample belonging to class 1 and a minus (negative) sign for a sample belonging to class 2. Accordingly, the class of each sample is determined based only on whether the value of the discriminate score is positive or negative. The magnitude (absolute value) of the discriminant score is by no means a measure of the magnitude or intensity of the property of the classification target. However, since the discriminant score $Y(k)$ is calculated by substituting the parameter values determined for each sample into the equation (1), the relationship between each sample based on the discriminant score $Y(k)$ is fixed.

As depicted in FIG. 2, the misclassified samples 1 and 2 tend to cluster in the vicinity of the decision surface S. That is, the misclassified samples 1 and 2 tend to occur in the region where the distance of each sample from the decision surface S is small. As the distance from the decision surface S increases, the frequency of occurrence of misclassified samples decreases. The discriminant score $Y(k)$ represents the distance of the sample from the decision surface S; therefore, as the discriminant score increases in absolute terms, the probability of misclassification decreases. That is, the discriminant score may be considered a measure of the likely correctness of the classification.

On the other hand, when obtaining the predicted value of the dependent variable for a sample for which the value of the dependent variable is unknown, that is, when predicting the class to which the unknown sample belongs, the values of the explanatory variables are calculated for the unknown sample, and these values are substituted into the equation (1) to determine the value of Y. Then, the class to which the unknown sample belongs is determined according to the sign of the value Y. For example, if the value of Y is positive, the unknown sample is assigned to class 1, but if the value of Y is negative, the unknown sample is assigned to class 2.

In this case, as is apparent from FIG. 2, if the absolute value of the discriminant score Y(k) is large, it is presumed that the position 10a of the unknown sample in the pattern space is sufficiently far from the decision surface S. It is therefore presumed that the prediction result in this case is correct. On the other hand, if the absolute value of the discriminant score Y(k) is small, it is presumed that the position 10b of the unknown sample in the pattern space is not sufficiently far from the decision surface S. As a result, the position 10b of the unknown sample is highly likely to lie in the misclassified-sample region C, and hence, the reliability of the prediction result is low.

It is therefore important to identify the misclassified-sample region C in order to determine whether the prediction made about the unknown sample 10a, 10b is correct or not. The present inventor has previously proposed, as one technique of the KY method, a method for generating a prediction model that achieves a classification rate of nearly 100% by determining the misclassified-sample region C on the basis of the discriminant scores of training samples and by performing discriminant analysis once again on the results (PCT/2007/074334).

According to this method, the discriminant score of each individual training sample in a training sample set is calculated based on the discriminant function obtained for the training sample set, and the class to which each individual training sample belongs is predicted. Then, the predicted class is compared with the class determined based on the measured value, and if they do not match, it is determined that the sample is a misclassified sample. The largest and smallest discriminant scores are detected from among such misclassified samples, and the region bounded by the largest and smallest discriminant scores is determined as the misclassified-sample region C. Once the misclassified-sample region C is determined, it can be identified whether the prediction made about the unknown sample 10a, 10b based on its discriminant score is correct or not.

In this method, when one discriminant function is obtained, the discriminant score of each individual training sample has to be calculated and, at the same time, the calculated value has to be compared with the measured value to identify whether the training sample is a misclassified sample or a correctly classified sample. Further, since the probability of misclassification varies depending on the discriminant technique employed, it is not possible to correctly determine the misclassified-sample region C. In view of this, the present inventor determined that if the classification/prediction can be performed without determining the misclassified-sample region C, not only can the prediction process be simplified but the prediction accuracy improves.

Misclassified samples cluster near the decision surface S with a high probability. On the other hand, as the discriminant score moves farther away from the decision surface S (Y=0), the sample classification/prediction accuracy increases. As can be seen from FIG. 2, the sample having the largest discriminant score Pmax and the sample having the smallest discriminant score Pmini are correctly classified samples. Samples located in the neighborhood of these samples are also correctly classified samples or are highly likely to be correctly classified samples. Accordingly, when predicting the class of an unknown sample based on its discriminant score, if the discriminant score R of the unknown sample is (as indicated at point Ra) not smaller than the largest discriminant score Pmax among the training samples or (as indicated at point Rb) not larger than the smallest discriminant score Pmini taken among the training samples, then it can be predicted that the unknown sample definitely belongs to class 1 or class 2, respectively.

Accordingly, when the discriminant score R of the unknown sample is not smaller than the largest discriminant score Pmax among the training samples or not larger than the smallest discriminant score Pmini taken among the training samples, it is determined that the class prediction based the discriminant score is correct, otherwise it is determined that the class prediction is not correct; in this way, the class to which the unknown sample belongs can be predicted with high accuracy.

Figure 3:
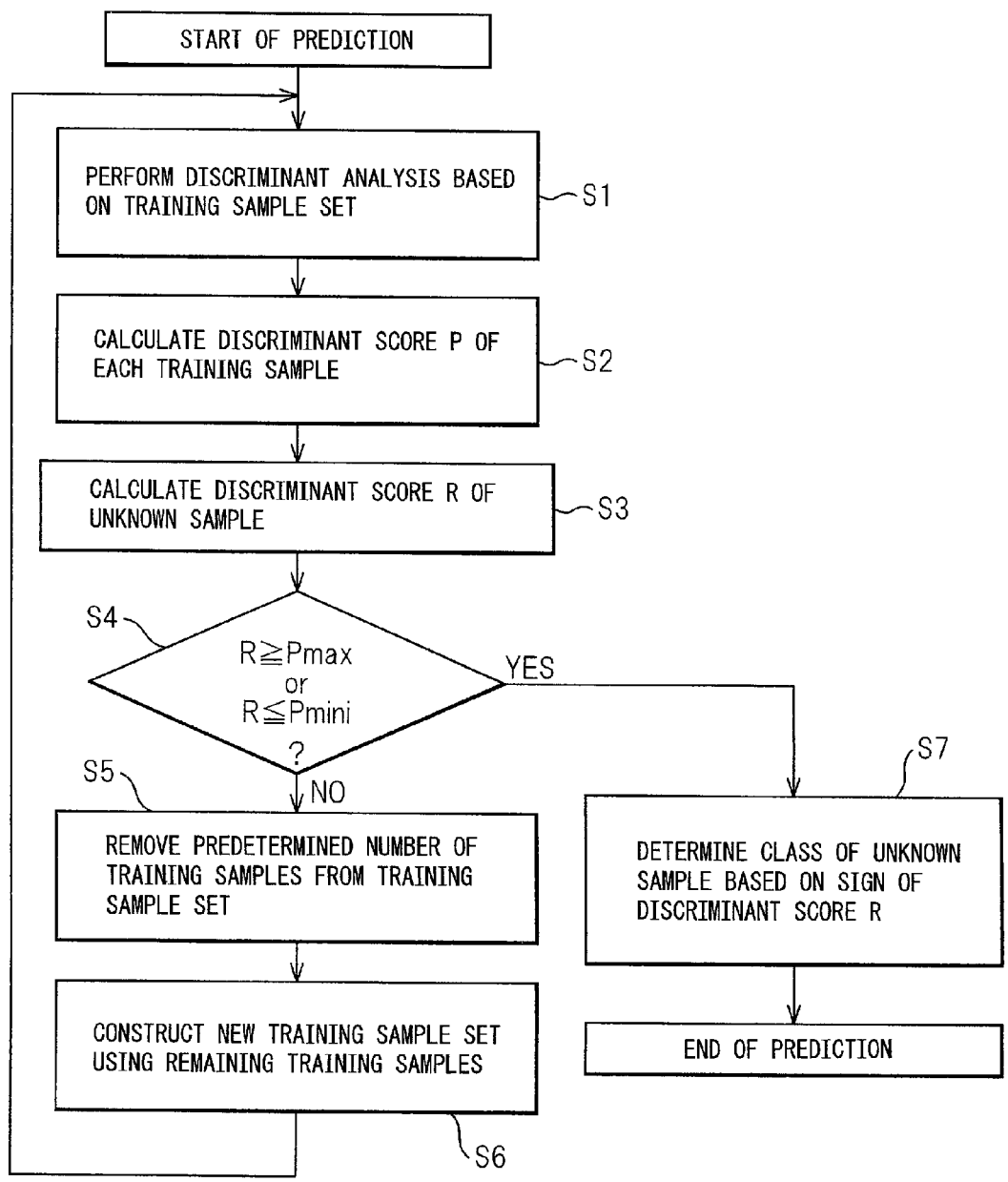
FIG. 3 is a flowchart illustrating a basic procedure for implementing a method for predicting the class of an unknown sample.

FIG. 3 is a flowchart illustrating a basic procedure for predicting the class of an unknown sample in a model-free manner by using a criterion for judging the correctness of the prediction such as described above. While FIG. 3 illustrates the procedure for predicting the class of one unknown sample in a model-free manner, the flowchart can be easily applied to the case where the classes of a plurality of unknown samples are predicted concurrently.

First, in step S1, a plurality of training samples for which the measured value of the dependent variable of each is known, i.e., samples each known to belong to class 1 or class 2, are prepared and entered into a discriminant analysis system for two-class discriminant analysis. In the next step S2, the discriminant score of each training sample is calculated by using the discriminant function generated by the discriminant analysis performed in step S1. In step S3, the discriminant score of a sample for which the value of the dependent variable is unknown is calculated by using the same discriminant function. In step S4, the discriminant scores calculated in steps S2 and S3 are sorted in increasing or decreasing order of the score, and the discriminant score R of the unknown sample is compared with the largest discriminant score Pmax and smallest discriminant score Pmini taken among the training samples. If it is determined as a result of the comparison that the discriminant score R of the unknown sample is not smaller than the largest discriminant score Pmax or not larger than the smallest discriminant score Pmini taken among the training samples (YES in step S4), then in step S7 the unknown sample is assigned to one or the other of the classes according to the sign of the discriminant score R of the unknown sample, after which the prediction process is terminated.

On the other hand, if it is determined in step S4 that the discriminant score R of the unknown sample is smaller than the largest discriminant score Pmax among the training samples but larger than the smallest discriminant score Pmini (NO in step S4), then the process proceeds to step 5, where a certain number of training samples are removed from the training sample set, and a new sample set is constructed.

The training samples to be removed here may be determined 1) by specifying m samples in decreasing order of the discriminant score starting from the sample having the largest discriminant score and n samples in increasing order of the discriminant score starting from the sample having the smallest discriminant score. In this case, m may or may not be equal to n. Further, the values of m and n may be determined by considering the size of the class population. Alternatively, the training samples to be removed here may be determined 2) by selecting samples whose discriminant scores fall, for example, within a range of 100% to 90% when the largest or smallest discriminant score is denoted as 100%. If the number m or n is set too large, the range of the samples to be removed may run off the edge of the region near the largest or smallest discriminant score sample and overlap into the misclassified-sample region. It is therefore preferable to hold the number to 10% or less of the total number of training samples, and more preferably to a few percent of the total number.

If the classification/prediction is to be performed with the highest accuracy, the total number of samples to be removed in step S4 is two, i.e., the sample having the largest discriminant score and the sample having the smallest discriminant score. Therefore, in step S4, at least two samples, one having the largest discriminant score and the other having the smallest discriminant score, are removed. In FIG. 3, if the maximum number of times that the process from step S1 to step S6 to be described later is to be repeated is preset in the system, the number of samples to be removed in each discriminant analysis cycle may be determined based on this maximum number of times. For example, if the total number of samples is 1000, and the maximum number of repetitions is preset to 100, then if 10 samples are removed in each discriminant analysis cycle, all the samples can be removed by repeating the discriminant analysis process 100 times.

In step S6 of FIG. 3, a new training sample set is constructed using the remaining training samples, after which the process returns to step S1 to repeat the discriminant analysis. In this case, since the training sample set is different from the initial training sample set, a new combination of explanatory variables (final parameter set) is selected as a result of feature extraction, and thus a new discriminant function is obtained that is different from the discriminant function obtained in the first discriminant analysis. As a result, the pattern space obtained in the second discriminant analysis is different from that obtained in the first discriminant analysis. Further, the discriminant score of each training sample and the discriminant score of the unknown sample are also different from those obtained in the first discriminant analysis.

Therefore, in step S4, a comparison between the unknown sample and the training samples is made based on the discriminant scores newly calculated for them. If YES in step S4, then in step S7 the class to which the unknown sample belongs is determined according to the sign of its discriminant score. If NO in step S4, the process proceeds to step S5.

By repeating the process from step S1 to step S6 until the answer to step S4 becomes YES, as described above, the class of the unknown sample can be accurately predicted without having to determine the misclassified-sample region (gray zone). The maximum number of repetitions may be preset in the system.

In the prior art classification/prediction method, the classification rate and the prediction rate drop as the number of training samples increases. By contrast, according to the method of FIG. 3, even when the number of training samples increases, the class of the unknown sample can be predicted without causing a degradation of prediction accuracy, by just increasing the number of times that the process from step S1 to step S6 is to be repeated. Accordingly, even when tens or hundreds of thousands of chemical data have been accumulated through implementation of the REACH regulation, the class of any unknown sample can be predicted by using all of these data as training samples while maintaining high prediction accuracy.

A first embodiment will be described below. In this embodiment, each sample is a chemical compound, and the dependent variable to be predicted is the result of Ames testing, active (+, mutagen) or inactive (−, non-mutagen).

Figure 4:
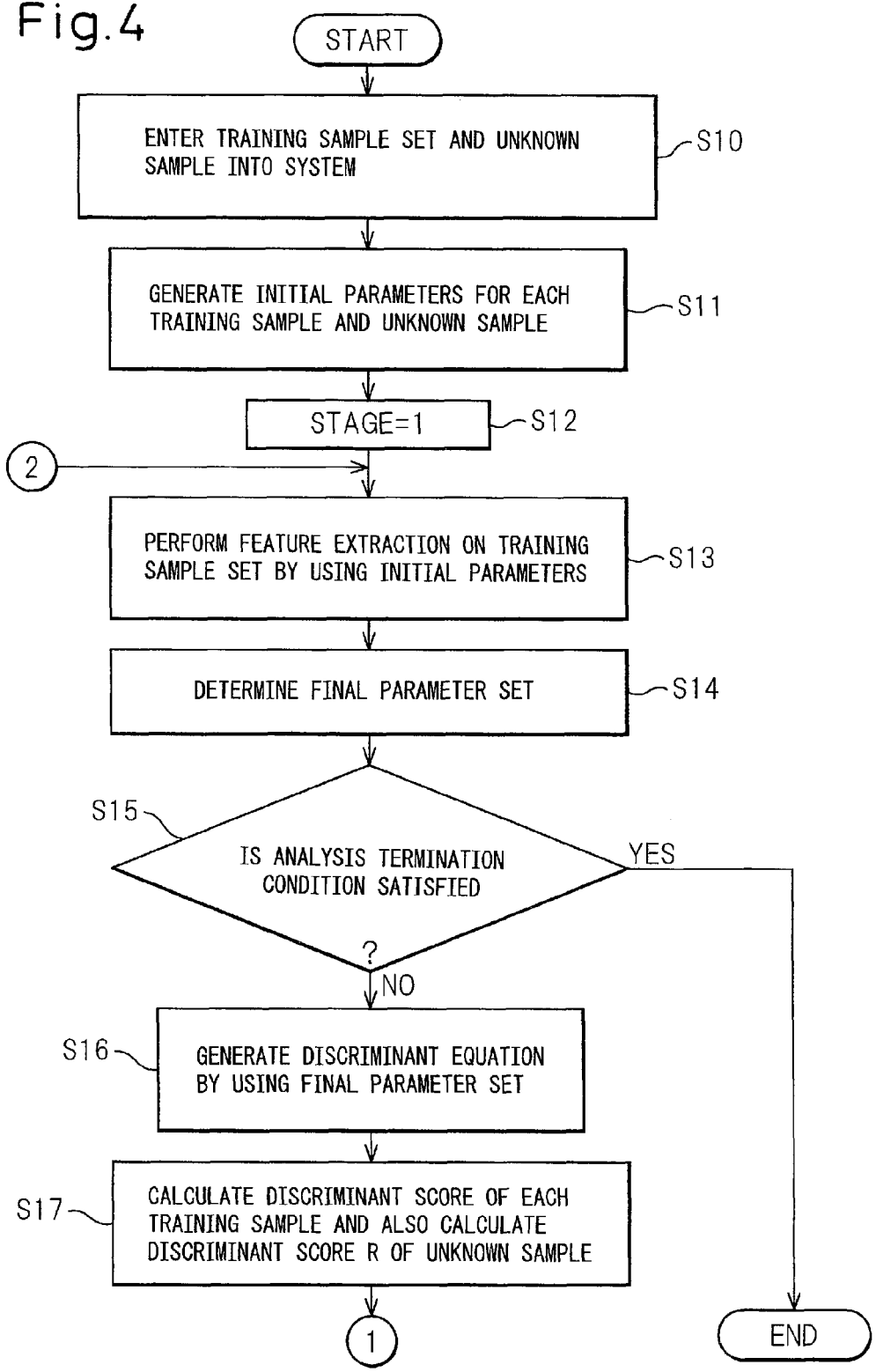
FIG. 4 is a flowchart illustrating the first half of a processing procedure according to one embodiment.
Figure 5:
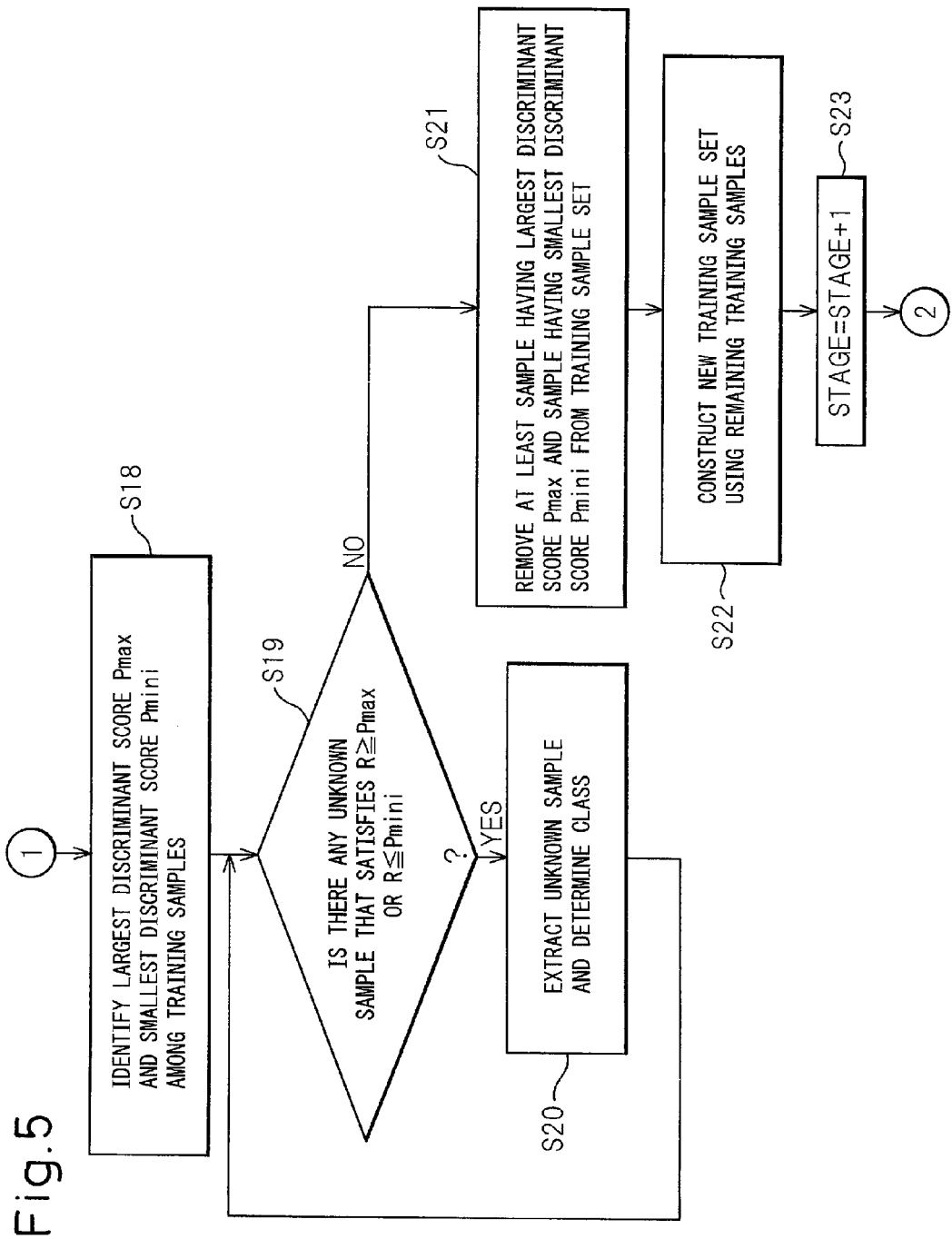
FIG. 5 is a flowchart illustrating the second half of the processing procedure according to the one embodiment depicted in FIG. 4.

FIGS. 4 and 5 are flowcharts illustrating a procedure for predicting the result of Ames testing, active or inactive, for a chemical compound. First, in step S10, a training sample set and an unknown sample as a chemical compound to be predicted are prepared and entered into a system. The training sample set is constructed from a plurality of chemical compounds whose measured values indicating the result of the Ames test, active or inactive, are known. The unknown sample is a chemical compound whose measured value indicating the result of the Ames test, active or inactive, is unknown. One or a plurality of samples may be prepared as unknown samples.

The training samples are entered in the form of one-, two-, or three-dimensional structural formulas into a sample class prediction apparatus, and a table such as depicted in FIG. 6 is constructed to store the sample data. In FIG. 6, column 60 indicates the two- or three-dimensional structural formula of each chemical compound as a sample. Column 61 indicates the CAS number of each chemical compound, and column 62 indicates the result of the Ames test. In column 62, "mutagen" means that the Ames test result indicates that the sample has mutagenicity (+), while "nonmutagen" means that the sample does not have mutagenicity (−). The data table in the illustrated example is used to classify the samples into two classes by classifying mutagenic samples as belonging to class 1 (positive class) and nonmutagenic samples as belonging to class 2 (negative class). Column 63 indicates the sample number. A similar table is constructed for the unknown samples, but column 62 for carrying the measured values of the Ames test is left blank.

Next, in step S11 of FIG. 4, initial parameters, i.e., explanatory variables $(x1, x2, \ldots, xx)$ for calculating the dependent variable, are generated. The initial parameters can be automatically generated from the structure of each chemical. For example, ADMEWORKS-ModelBuilder (registered trademark) marketed by Fujitsu can automatically generate about 800 parameters based on the two- or three-dimensional structural formulas and various properties of chemicals. The initial parameters are generated for the unknown sample as well as for each training sample. In step S12, STAGE is set to 1 to initiate the first discriminant analysis.

In step S13, feature extraction is performed on the training samples by using the initial parameters, and noise parameters unwanted for classification are removed. The final parameter set $(x1, x2, \ldots, xn)$ is thus determined (step S14). The feature extraction can be performed using known techniques such as simple correlation coefficient, multiple correlation coefficient, frequency of occurrence, Fischer ratio, analysis of variance, etc. Various engines for feature extraction are commercially available.

FIG. 7 is a table depicting the final parameter set selected, as a result of the feature extraction, as having effects on the Ames test results, and numerical data for the respective parameters for each individual chemical compound. Column 70 indicates the structural formula of each chemical compound, and column 71 and subsequent columns indicate the various parameters. For example, column 71 indicates the molecular mass of each chemical compound, column 72 indicates the molecular surface area, and column 73 indicates the value of log P, as the respective parameters. In the data table, the value carried in cell 74 indicates the molecular mass of sample 1, the value in cell 75 indicates the molecular surface area of sample 1, and the value in cell 76 indicates the value of log P of sample 1. The values carried in the respective cells provide the parameter data for the corresponding sample. Column 77 indicates the sample number of each sample.

In step S14, it is determined whether the condition for terminating the analysis is satisfied or not. It is determined that the analysis termination condition is satisfied, for example, when there is no longer any unknown sample whose class is yet to be assigned (predicted), or when the number of stages has reached a preset maximum number or the number of samples in the training sample set has decreased to or below a preset minimum number, or when the reliability metric has decreased to or below a predetermined value. Here, the reliability metric is defined by the value obtained by dividing the number of samples by the number of parameters; if this value is small, the discriminant equation generated using the samples and the parameters has hardly any scientific or data analytic meaning, and it is determined that the analysis has failed. In usual analysis, this value is set to 4, and as the value becomes larger than 4, the reliability of the discriminant equation becomes correspondingly higher.

Figure 8:
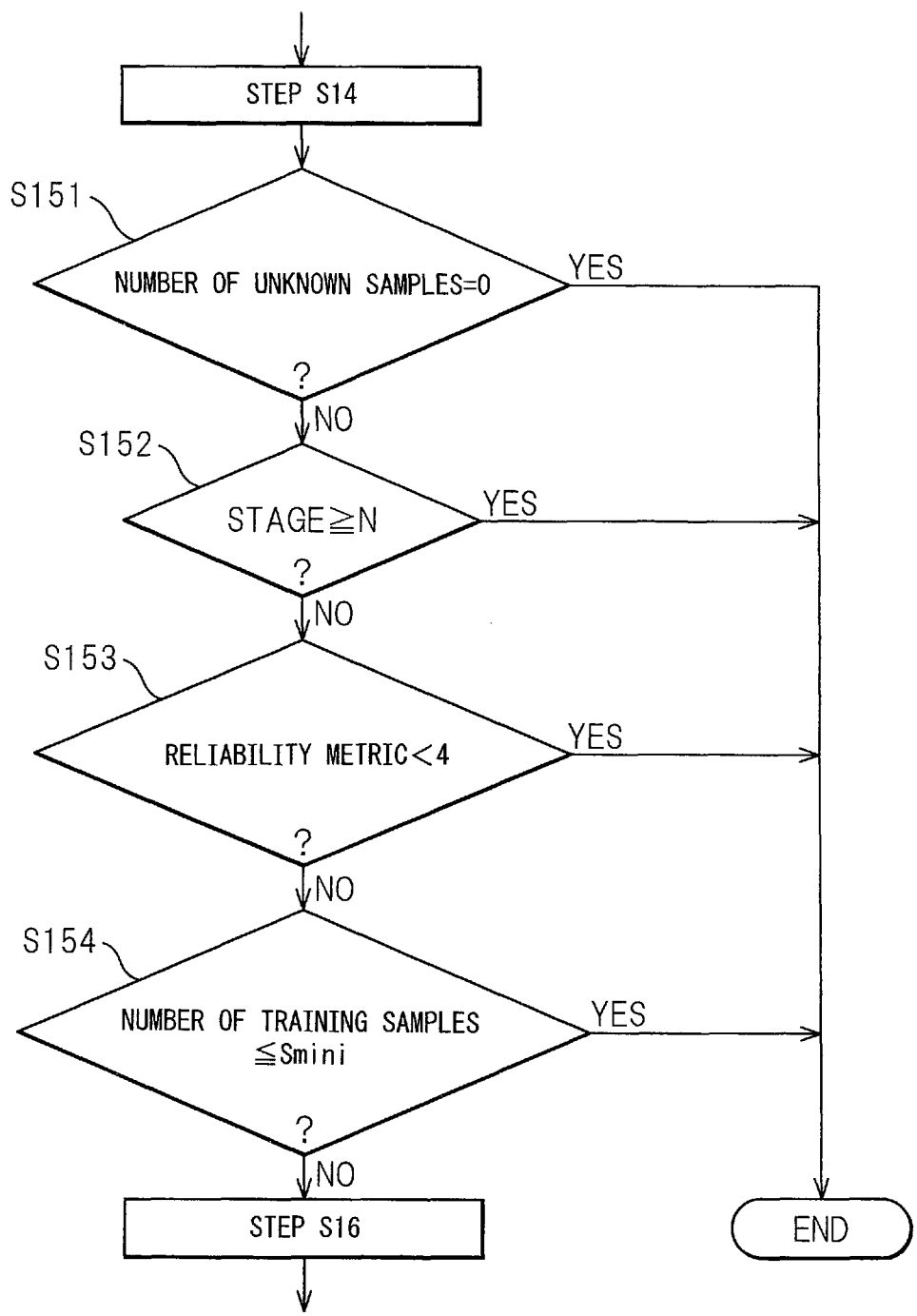
FIG. 8 is a diagram illustrating the details of one step in FIG. 4.

FIG. 8 illustrates the details of step S15. The process from step S151 to step S154 corresponds to the step S15 in FIG. 4. First, in step S151, it is verified whether there is any unknown sample remaining to be predicted. If there is no such unknown sample (YES in step S151), the prediction process is terminated. In step S152, it is determined whether the number of stages up to the current stage has reached the preset maximum number of stages, N. If the number of stages has reached N (YES in step S152), the process is terminated.

In step S153, it is determined whether the value of the reliability metric, which is determined by the number of samples and the number of parameters, has dropped below 4. If the reliability metric has dropped below 4 (YES in step S153), the process is terminated. In step S154, it is determined whether the number of samples has decreased to or below the preset minimum number of samples, Smini. If it has decreased to or below the minimum number of samples (YES in step S154), the process is terminated.

Accordingly, in the illustrated embodiment, if none of the above termination conditions are satisfied, the process proceeds to step S16. Here, the order of steps S151 to S154 may be changed as desired, and steps S152, S154, etc. may be omitted. Further, a step for limiting the processing time may be inserted in place of or in addition to step S152.

Turning back to FIG. 4, if the termination condition is satisfied in step S15 (YES in step S15), the analysis process is terminated. If the termination condition is not satisfied in step S15 (NO in step S15), the process proceeds to step S16 where the discriminant equation for the first stage (STAGE 1) is generated using the final parameter set. In the discriminant analysis, the discriminant function is expressed by the earlier given equation (1).

In step S17, the discriminant score of each training sample is calculated by using the thus generated discriminant function, and the discriminant score of the unknown sample is also calculated by using the same discriminant function. The discriminant score Yk of the k-th sample is calculated as $$Yk = a1x1k \pm a2x2k \pm \ldots \pm anxnk \pm C \qquad (2)$$

where x1k, x2k, ..., xnk are parameter data (explanatory variable data) for the k-th sample, and a1, a2, a3, ..., an are the weighting coefficients of the respective parameters, and are common to all the samples. C is a constant.

The parameter data x11, x21, x31, etc., are obtained from the data carried in the respective cells in FIG. 7. Accordingly, when the coefficients a1, a2, etc., of the respective parameters are obtained by the discriminant analysis, the discriminant score Yk of the k-th sample is calculated by substituting the data carried in the respective cells of the table of FIG. 7 into the equation (2).

In step S18 of FIG. 5, the largest discriminant score Pmax and the smallest discriminant score Pmini are identified among the training samples by sorting all the training samples according to their discriminant scores Yk. In step S19, the discriminant score R of each unknown sample calculated in step S17 is compared with the largest discriminant score Pmax and the smallest discriminant score Pmini, to see whether the unknown sample satisfies the condition R≥Pmax or R≤Pmini. If, of the plurality of unknown samples, there is any unknown sample that satisfies R≥Pmax or R≤Pmini (YES in step S19), that sample is extracted and assigned to one or the other of the classes according to the sign of its discriminant score (step S20).

Next, the process returns to step S19 to see whether there is any other unknown sample that satisfies R≥Pmax or R≤Pmini. The process from steps S19 to S20 is iteratively performed until it is determined in step S19 that there is no longer any unknown sample that satisfies R (discriminant score of unknown sample)≥Pmax or R≤Pmini. In this way, in step S20, all the unknown samples that satisfy R≥Pmax or R≤Pmini in the current stage are extracted, and their classes are determined.

If NO in step S19, the process proceeds to step S21 where samples having large discriminant scores or small discriminant scores are removed from each class of the training sample set in accordance with a sample removal rule. The sample removal rule may be selected from among the rules described with reference to FIG. 3, or may be suitably specified by the user. In step S22, the remaining training samples are grouped together to construct a new training sample set. In step S23, STAGE is incremented by 1, i.e., STAGE=2, and after that, the process starting from step S13 in FIG. 4 is performed to classify the unknown samples in the second stage (to determine the class to which each unknown sample belongs).

When the class assignment of all the unknown samples is completed by iteratively performing the process from step S13 to step S23 as described above, the analysis termination condition is satisfied in step S15, whereupon the classification/prediction process is terminated. In this case, since the process for determining the class of each unknown sample is performed when the discriminant score of the unknown sample is not smaller than the largest discriminant score Pmax or not larger than the smallest discriminant score Pmini, the reliability of the prediction is very high.

In the above process, the same discriminant analysis technique may be used for all the stages, or different techniques may be used for different stages. For example, provisions may be made to use a Bayes discriminant analysis method in STAGE 1 and an AdaBoost method in STAGE 2. Further, the same number of samples may be removed in each stage, or a different number of samples may be removed in each different stage. For example, provisions may be made to remove a relatively large number of samples in a relatively early stage and a smaller number of samples in a higher order stage.

According to the above method, the class of each unknown sample can be predicted with high accuracy in a model-free manner. Further, the computation time for performing the prediction can be significantly reduced since there is no need to classify the training samples into misclassified samples and correctly classified samples.

Figure 9:
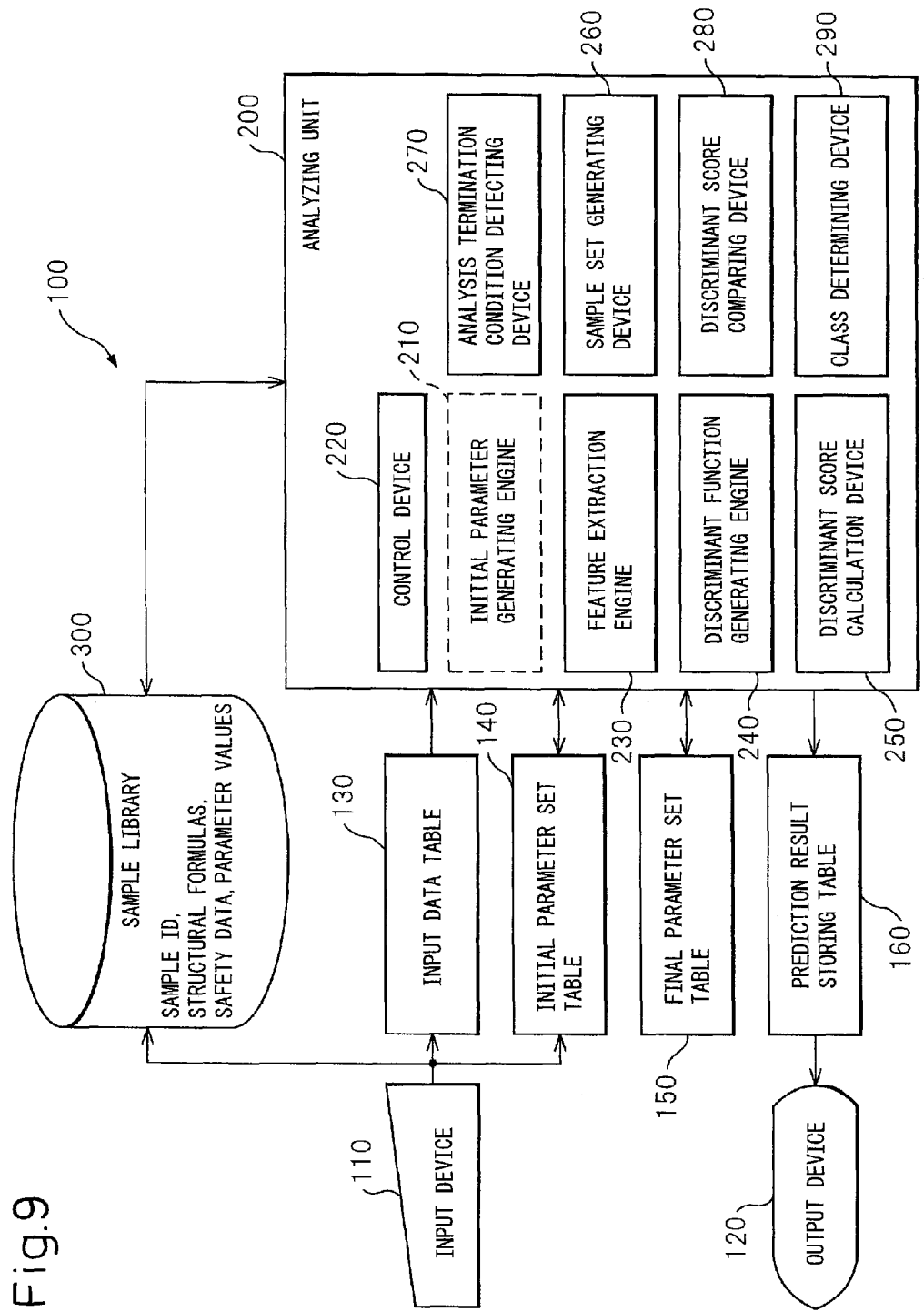
FIG. 9 is a block diagram illustrating the general configuration of a property prediction apparatus according to one embodiment.

FIG. 9 is a block diagram illustrating the general configuration of a sample class prediction apparatus according to a third embodiment. The prediction apparatus 100 according to the present embodiment includes an input device 110 for entering training sample data and unknown sample data and an output device 120 for outputting the prediction result of an unknown sample or data needed during processing. When each sample is a chemical compound, the one- or two-dimensional structural formula of the chemical compound and its known dependent variable value (i.e., information identifying its class, i.e., class 1 or class 2, for example, safety data) are entered from the input device 110 and stored in an input data table 130. When entering an unknown sample, the value of the dependent variable is not entered.

Initial parameter set data may be entered via the input device 110 and stored in an initial parameter set table 140. If an analyzing unit 200 has an engine 210 for automatically generating the initial parameters for input samples, there is no need to enter the initial parameter set data from the input device 110.

In FIG. 9, reference numeral 150 is a table for storing the final parameter set obtained by performing feature extraction on the initial parameter set. Further, reference numeral 160 is a prediction result storing table for storing class assignment information, i.e., prediction result information for unknown samples. Usually, these tables 130, 140, 150, and 160 are stored in one storage device.

The analyzing unit 200 includes a control device 220, an initial parameter generating engine 210, a feature extraction engine 230, a discriminant function generating engine 240, a discriminant score calculation device 250, a sample set generating device 260, an analysis termination condition detecting device 270, a discriminant score comparing device 280, and a class assignment implementing device 290. If provisions are made to generate the initial parameters outside the apparatus, the initial parameter generating engine 210 is not needed. When the sample is a chemical compound, the initial parameter generating engine 210 generates a plurality of structure descriptors based on the chemical structural formula entered from the input device 110. Reference numeral 300 is a sample library in which the structural formulas, safety data, initial parameter values, etc. of the training samples previously used for the prediction of properties are stored as library data.

The feature extraction engine 230 determines the final parameter set by performing feature extraction on the initial parameter set, and stores it in the final parameter set table 150. The discriminant function generating engine 240 includes various known discriminant analysis engines and, using the discriminant analysis engine suitably specified by the user or suitably selected by the system, generates the discriminant function by performing the discriminant analysis of the input sample while referring to the final parameter set table 150. The discriminant score calculation device 250 calculates the discriminant score of each sample by entering the parameters of the sample into the discriminant function generated by the discriminant function generating engine 240. The sample set generating device 260 constructs a new training sample set by removing samples having large discriminant scores or samples having small discriminant scores from the training sample set in accordance with a predetermined sample removal rule.

The feature extraction engine 230, the discriminant function generating engine 240, the discriminant score calculation device 250, and the new sample set generating device 260 operate under the control of the control device 220 to carry out the process illustrated in FIGS. 4 and 5. The analysis termination condition detecting device 270 terminates the analysis process when one of the following conditions is satisfied: 1) the number of unknown samples for which the class to which each belongs is to be predicted has decreased to zero; 2) the number of repetitions of the process has exceeded a predetermined number (or the processing time has exceeded a predetermined time); 3) the number of samples contained in the newly constructed training sample set has decreased to or below a predetermined number; and 4) the reliability metric has decreased to or below a predetermined value.

The discriminant score comparing device 280 compares the discriminant score R of each unknown sample with the largest discriminant score Pmax or the smallest discriminant score Pmini taken among the training samples. The class determining device 290 carries out the class assignment of the unknown sample based on the result supplied from the discriminant score comparing device 280. That is, if the discriminant score R of the unknown sample is not smaller than the largest discriminant score Pmax or not larger than the smallest discriminant score Pmini taken among the training samples, the unknown sample is assigned to one or the other of the classes according to the sign of its discriminant score R; otherwise, no class assignment is made. The result from the discriminant score comparing device 280 is temporarily stored in the prediction result storing table 160 and thereafter output in a suitable format via the output device 120. The output device can be selected from among various kinds of storage devices, a display, a printer, etc., and the output format can be suitably selected from among various kinds of files (for example, USB file), display, printout, etc.

Each of the above programs can be stored on a computer-readable recording medium, and such recording media can be distributed and circulated for use. Further, each of the above programs can be distributed and circulated through communication networks such as the Internet. The computer-readable recording media include magnetic recording devices, optical disks, magneto-optical disks, or semiconductor memories (such as RAM and ROM). Examples of magnetic recording devices include hard disk drives (HDDs), flexible disks (FDs), magnetic tapes (MTs), etc. Examples of optical disks include DVDs (Digital Versatile Discs), DVD-RAMS, CD-ROMs, CR-RWs, etc. Examples of magneto-optical disks include MOs (Magneto-Optical discs).

The training sample data entered via the input device 110 and the initial parameter set data generated for the training sample are stored via the analyzing unit 200 into the sample library. Accordingly, using the sample library 300, the class to which each unknown sample belongs can be predicted by just entering the structural formula data of the unknown sample via the input device 100. Further, when new training sample data becomes available, the most up-to-date training sample set can be constructed by entering the data from the input device 100 into the class prediction apparatus 100 and adding the data to the training sample data currently stored in the sample library 300. The class prediction is performed by using the most up-to-date training sample set as the initial sample set. The apparatus can thus predict the property of any unknown sample by using the database constantly updated by adding new training sample data.

The input device 110 and the output device 120 may together be constructed from a display device equipped with an interactive graphical user interface. In this case, provisions may be made to allow the user to perform operations such as the selection of the analysis termination condition, the selection of the sample removal rule, etc., by interacting with a computer via the display screen.

INDUSTRIAL APPLICABILITY

The method, program, and apparatus disclosed in this specification are applicable to any industrial field to which two-class classification can be applied. The main application fields are listed below.

1) Chemical data analysis
2) Biotechnology-related research
3) Protein-related research
4) Medical-related research
5) Food-related research
6) Economy-related research
7) Engineering-related research
8) Data analysis aimed at improving production yields, etc.
9) Environment-related research In the field of chemical data analysis 1), the invention can be applied more particularly to the following researches.

(1) Structure-activity/ADME/toxicity/property relationships research
(2) Structure-spectrum relationships research
(3) Metabonomics-related research
(4) Chemometrics research For example, in the field of structure-toxicity relationship research, it is extremely important to predict Ames test results. The reason is that the Ames test is incorporated as one of the most important items into national-level chemical regulations such as industrial safety and health law and chemical examination law related to toxic chemicals regulations. Any chemical to be marketed is required to pass the Ames test; otherwise, the chemical could not be manufactured in Japan, and the manufacturing activities of chemical companies would halt. Further, manufacturing overseas and exports of such chemicals are banned by safety regulations adopted in the countries concerned.

According to the REACH regulation adopted by the EU Parliament, any company using a chemical is obliged to predict and evaluate the Ames test result of that chemical. The present invention provides a very useful tool for the prediction of such test results. The Ames test is one of the mutagenesis tests developed by Dr. Ames of USA, and provides a simple method for testing carcinogenicity. The Ames test is therefore widely used to measure the safety of many chemicals and products using chemicals.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A sample class classification/prediction method, comprising performing operations in a programmed processor, the operations including:
   constructing a set of training samples, each sample including a plurality of explanatory variables and a measured value indicating whether the sample belongs to a first known class or a second known class;
   constructing an unknown sample set of at least one unknown sample, each sample including a plurality of explanatory variables;
   obtaining a discriminant function that assigns training samples to a first predicted class or a second predicted class on the basis of the plurality of explanatory variables and the measured value;
   calculating the ratio of the number of training samples to the number of parameters in the discriminant function, thereby calculating a reliability metric;
   terminating the classification/prediction if the reliability metric is less than a predetermined threshold or if the unknown sample set is empty, and otherwise
   calculating a discriminant score for each of the training samples and a discriminant score for an each of the unknown samples by using said discriminant function;
   selecting a plurality of unknown samples having a discriminant score greater than the largest discriminant score of the training sample set, assigning these selected unknown samples to the first predicted class, and removing these selected samples from the unknown sample set;
   selecting a plurality of unknown samples having a discriminant score less than the smallest discriminant score of the training sample set, assigning these selected unknown samples to the second predicted class, and removing these selected samples from the unknown sample set;
   constructing a new set of training samples by removing at least the training sample having the largest discriminant score and the training sample having the smallest discriminant score; and
   repeating the steps of obtaining a discriminant function through constructing a new set of training samples.

2. The method of claim 1, further comprising performing feature extraction to remove unwanted explanatory variables prior to obtaining the discriminant function.

3. The method of claim 1, wherein said constructing a new set of training samples is performed by removing a first number of training samples having the largest discriminant scores and a second number of training samples having the smallest discriminant scores.

4. The method of claim 3, wherein said first number and said second number are determined based on the ratio of the number of training samples whose measured values indicate said first class to the number of training samples whose measured values indicate said second class in said set of training samples.

5. The method of claim 1, wherein each of the training samples and each of the at least one unknown sample is a chemical compound, and wherein said first known class indicates that the compound has a given toxicity and said second known class indicates that the compound lacks said toxicity.

6. The method of claim 1, wherein the value of the predetermined threshold is four.

7. A non-transitory computer readable medium having a program recorded thereon, wherein said program, when executed, causes a processor to perform a method comprising:
   constructing a set of training samples, each sample including a plurality of explanatory variables and a measured value indicating whether the sample belongs to a first known class or a second known class;
   constructing an unknown sample set of at least one unknown sample, each sample including a plurality of explanatory variables;
   obtaining a discriminant function that assigns training samples to a first predicted class or a second predicted class on the basis of the plurality of explanatory variables and the measured value;

calculating the ratio of the number of training samples to the number of parameters in the discriminant function, thereby calculating a reliability metric;

terminating the classification/prediction if the reliability metric is less than a predetermined threshold or if each of the at least one unknown sample in the unknown sample set has been assigned to a predicted class, and otherwise calculating a discriminant score for each of the training samples and a discriminant score for each of the unknown samples by using said discriminant function;

selecting a plurality of unknown samples having a discriminant score greater than the largest discriminant score of the training sample set, assigning these selected unknown samples to the first predicted class, and removing these selected samples from the unknown sample set;

selecting a plurality of unknown samples having a discriminant score less than the smallest discriminant score of the training sample set, assigning these selected unknown samples to the second predicted class, and removing these selected samples from the unknown sample set;

constructing a new set of training samples by removing at least the training sample having the largest discriminant score and the training sample having the smallest discriminant score; and repeating the steps of obtaining a discriminant function through identifying the class to which the unknown sample belongs or constructing a new set of training samples.

8. The non-transitory computer-readable medium of claim 7, wherein the program, when executed, further causes the processor to perform feature extraction to remove unwanted explanatory variables prior to obtaining the discriminant function.

9. The non-transitory computer-readable medium of claim 7, wherein the processor constructs said new set of training samples by removing a first number of training samples having the largest discriminant scores and a second number of training samples having the smallest discriminant scores.

10. The non-transitory computer-readable medium of claim 9, wherein the processor determines said first number and said second number based on the ratio of the number of training samples whose measured values indicate said first class to the number of training samples whose measured values indicate said second class in said set of training samples.

11. The non-transitory computer-readable medium of claim 7, wherein each of the training samples and each unknown sample is a chemical compound, and wherein said first known class indicates that the compound has a given toxicity and said second known class indicates that the compound lacks said toxicity.

12. The non-transitory computer-readable medium of claim 7, wherein the value of the predetermined threshold is four.

13. A sample class classification/prediction apparatus, comprising:

a memory storing a predetermined threshold; and at least one processor programmed to construct a set of training samples, each sample comprising a plurality of explanatory variables and a measured value indicating whether the sample belongs to a first known class or a second known class;

construct an unknown sample set, each sample comprising a plurality of explanatory variables;

obtain a discriminant function that assigns training samples to a first predicted class or a second predicted class on the basis of the plurality of explanatory variables and the measured value;

calculate the ratio of the number of training samples to the number of parameters in the discriminant function, thereby calculating a reliability metric;

terminate the classification/prediction if the reliability metric is less than the predetermined threshold or if each unknown sample in the unknown sample set has been assigned to a predicted class, and otherwise calculate a discriminant score for each of the training samples and a discriminant score for each of the unknown samples by using said discriminant function;

select a plurality of unknown samples having a discriminant score greater than the largest discriminant score of the training sample set, assign these selected unknown samples to the first predicted class, and remove these selected samples from the unknown sample set;

select a plurality of unknown samples having a discriminant score less than the smallest discriminant score of the training sample set, assign these selected unknown samples to the second predicted class, and remove these selected samples from the unknown sample set;

repeat the steps of obtaining a discriminant function through identifying the class to which the unknown sample belongs or constructing a new set of training samples.

14. The non-transitory computer-readable medium of claim 13, wherein the program, when executed, further causes the processor to perform feature extraction to remove unwanted explanatory variables prior to obtaining the discriminant function.

15. The non-transitory computer-readable medium of claim 13, wherein the processor constructs said new set of training samples by removing a first number of training samples having the largest discriminant scores and a second number of training samples having the smallest discriminant scores.

16. The non-transitory computer-readable medium of claim 15, wherein the processor determines said first number and said second number based on the ratio of the number of training samples whose measured values indicate said first class to the number of training samples whose measured values indicate said second class in said set of training samples.

17. The non-transitory computer-readable medium of claim 13, wherein each of the training samples and each unknown sample is a chemical compound, and wherein said first known class indicates that the compound has a given toxicity and said second known class indicates that the compound lacks said toxicity.

18. The non-transitory computer-readable medium of claim 13, wherein the value of the predetermined threshold is four.

* * * * *

UNITED STATES PATENT AND TRADEMARK OFFICE
CERTIFICATE OF CORRECTION

PATENT NO.         : 8,682,813 B2                                         Page 1 of 1
APPLICATION NO.    : 13/019683
DATED              : March 25, 2014
INVENTOR(S)        : Yuta It is certified that error appears in the above-identified patent and that said Letters Patent is hereby corrected as shown below:

In the Claims

Column 18, Lines 36-40, In Claim 14, delete "The non-transitory computer-readable medium of claim 13, wherein the program, when executed, further causes the processor to perform feature extraction to remove unwanted explanatory variables prior to obtaining the discriminant function." and insert -- The sample class classification/prediction apparatus of claim 13, wherein the processor further performs feature extraction to remove unwanted explanatory variables prior to obtaining the discriminant function. --, therefor.

Column 18, Lines 41-42, In Claim 15, delete "The non-transitory computer-readable medium of claim 13, wherein the processor constructs" and insert -- The sample class classification/prediction apparatus of claim 13, wherein the processor further constructs --, therefor.

Column 18, Line 47, In Claim 16, delete "The non-transitory computer-readable medium of claim 15, wherein the processor determines" and insert -- The sample class classification/prediction apparatus of claim 15, wherein the processor further determines --, therefor.

Column 18, Line 54, In Claim 17, delete "The non-transitory computer-readable medium" and insert -- The sample class classification/prediction apparatus --, therefor.

Column 18, Line 60, In Claim 18, delete "The non-transitory computer-readable medium" and insert -- The sample class classification/prediction apparatus --, therefor.

Signed and Sealed this
Twenty-third Day of September, 2014

Michelle K. Lee
*Deputy Director of the United States Patent and Trademark Office*